(12) United States Patent
Chaudhuri

(10) Patent No.: US 12,171,852 B1
(45) Date of Patent: Dec. 24, 2024

(54) COMPOSITION AND METHODS FOR REGULATING MELANOGENESIS

(71) Applicant: Sytheon Ltd, Parsippany, NJ (US)

(72) Inventor: Ratan K Chaudhuri, Lincoln Park, NJ (US)

(73) Assignee: Sytheon Ltd, Parsippany, NJ (US)

( * ) Notice: Subject to any disclaimer, the term of this patent is extended or adjusted under 35 U.S.C. 154(b) by 0 days.

(21) Appl. No.: 18/775,688

(22) Filed: Jul. 17, 2024

Related U.S. Application Data

(60) Provisional application No. 63/621,598, filed on Jan. 17, 2024, provisional application No. 63/527,483, filed on Jul. 18, 2023.

(51) Int. Cl.
| | | |
|---|---|---|
| *A61K 8/44* | (2006.01) | |
| *A61Q 17/04* | (2006.01) | |
| *A61Q 19/02* | (2006.01) | |
| *A61Q 19/08* | (2006.01) | |

(52) U.S. Cl.
CPC .............. *A61K 8/442* (2013.01); *A61Q 17/04* (2013.01); *A61Q 19/02* (2013.01); *A61Q 19/08* (2013.01); *A61K 2800/522* (2013.01); *A61K 2800/782* (2013.01)

(58) Field of Classification Search
None
See application file for complete search history.

(56) References Cited

U.S. PATENT DOCUMENTS

| | | | |
|---|---|---|---|
| 4,596,791 A | 6/1986 | Piwinski et al. | |
| 4,684,528 A | 8/1987 | Godfrey | |
| 4,758,439 A | 7/1988 | Godfrey | |
| 4,859,653 A * | 8/1989 | Morelle | A61K 8/65 514/564 |
| 5,582,817 A | 12/1996 | Otsu et al. | |
| 6,670,494 B1 | 12/2003 | Trusovs | |
| 7,427,690 B2 | 9/2008 | Gupta | |
| 7,572,933 B2 | 8/2009 | Gupta | |
| 8,247,398 B2 | 8/2012 | Goel | |
| 9,242,008 B2 | 1/2016 | Sciavolino et al. | |
| 10,638,785 B2 | 5/2020 | Wadhwa | |
| 10,905,670 B2 | 2/2021 | Factor et al. | |
| 10,966,949 B2 | 4/2021 | Dattilo et al. | |
| 11,649,252 B2 | 5/2023 | Kaufmann et al. | |
| 11,998,518 B2 | 6/2024 | Factor et al. | |
| 2008/0214649 A1 | 9/2008 | Yu | |
| 2023/0346732 A1 | 11/2023 | Factor et al. | |

FOREIGN PATENT DOCUMENTS

| | | |
|---|---|---|
| EP | 0178911 A2 | 4/1986 |
| HU | 200922 | 9/1990 |

OTHER PUBLICATIONS

Invitation to Pay Additional Fees, PCT/US2024/038356, International PCT patent application on co-pending US companion application.
Xue, Q et. al., "Functions and mechanisms of protein lysine butyrylation (Kbu): Therapeutic implications in human diseases", Genes and Diseases, v. 10., pp. 2479-2490, 2023.
Zhu, Z et. al., "Identification of lysine isobutyrylation as a new histone modification mark", Nucleic Acids Research, V. 49, No. 1, pp. 177-189, 2021.
Sawada, Y et. al., "Cutaneous innate immune tolerance is mediated by epigenetic control of MAP2K3 by HDAC8/9", Sci. Immunol. 6(59), May 21, 2021.
Gupta, D et. al., "Salts of Therapeutic Agents: Chemical, Physiochemical, and Biological Considerations", Molecules, v. 23, p. 1719, 2018.
Chen, Y et. al. "Lysine Propionylation and Butyrylation Are Novel Post-translational Modifications in Histones", Molecular & Cellular Proteomics 6.5, p. 812, 2007.
Pieper, R et. al., "Concentration and chemical form of dietary zinc shape the procine colon microbiome, its functional capacity and antibiotic resistance gene repertoire", The ISME Journal, 14:2783-2793, 2020.
Un-published co-pending application U.S. Appl. No. 18/775,629.
International Search Report and Preliminary Written Opinion for PCT/US2024/38362—PCT of current Application.
PubChem-CID-86653424, Create Date Feb. 2, 2015.
PubChem-CID-129729441, Create Date Sep. 13, 2013.

* cited by examiner

*Primary Examiner* — Nannette Holloman
(74) *Attorney, Agent, or Firm* — Hoffmann & Baron, LLP; Edward K Welch, II

(57) ABSTRACT

Zinc di-(dibutyryl lysinate) s, topical compositions comprising the same, and their use in skin lightening/brightening/even toning applications.

21 Claims, No Drawings

COMPOSITION AND METHODS FOR REGULATING MELANOGENESIS

RELATED APPLICATIONS

The present application claims the benefit of prior U.S. Provisional Patent Application Nos. 63/527,483, filed Jul. 18, 2023, entitled "Novel Amino Acid Based Histone Deacetylase Modulators for Treating Skin" and 63/621,598, filed Jan. 17, 2024, entitled "Compositions and Methods for Regulating Malanogenesis," the contents of both of which are hereby incorporated herein by reference in their entirety.

FIELD OF THE INVENTION

The present invention is directed to the novel compound zinc di-(dibutyryl lysinate) (INCI name zinc dibutyroylly-sinate), also referred to as Bis (N2, N6-dibutyryl-lysine) zinc salt (2:1), and its use in skin lightening/brightening/even toning applications as well as in the prevention, mitigation and/or reversal of the formation of sun-, laser therapy-, acne- and scar-induced hyper-pigmented spots as well as age spots, liver spots, freckles, melasma etc.

BACKGROUND

Human skin color is quite variable around the world. It ranges from a very dark brown among some Africans, Australians, and Asian-Indians to a near pinkish yellow among some northwest Europeans. There are no people who truly have black, white, red, or yellow skin. These are commonly used terminologies that do not reflect biological reality. Skin coloration in humans arises from a complex series of cellular processes that are carried out within that population of cells known as the melanocytes which are located in the lower part of the epidermis. These processes result in the synthesis and transfer of a pigment, melanin, which, besides being responsible for skin color and tone, is the key physiological defense against sun-induced damage, such as sunburn, photoaging and photo-carcinogenesis.

The mechanism by which melanin is produced is known as melanogenesis. So formed melanin is accumulated/deposited in melanosomes, vesicles found within the melanocyte cells, which are subsequently transferred from the melanocytes and taken up and internalized by the keratinocytes, which then carry them to the surface of the skin. Skin coloration is primarily regulated by the amount and type of melanin synthesized by the epidermal melanocyte. However, additional, and equally contributing factors include (a) the efficiency of the transfer of the melanosomes, hence the melanin, from the melanocytes to the neighboring keratinocytes and (b) the subsequent distribution and degradation of the transferred melanosomes by the recipient keratinocytes.

Environmental factors can also markedly affect skin color. For example, exposure of the skin to sun light markedly influences and increases the amount and rate of melanin production, most often producing a further darkening of the skin or a "tan." Conversely, exposure to other factors, especially agents that interfere with melanin production and/or the transfer of melanin, may result in a decrease of melanin production and/or the rate or efficiency of its transfer resulting in a lightening of the skin.

In melanocytes, MITF (microphthalmia-associated transcription factor) has a dominant role that has been termed 'master transcriptional regulator' of the melanocyte lineage (Hemesath et al, microphthalmia, a critical factor in melanocyte development, defines a discrete transcription factor family. *Genes Dev* 1994; 8:2770-2780; Nguyen and Fisher, MITF and UV responses in skin: from pigmentation to addiction, *Pigment Cell Melanoma Res*, 32 (2): 224-236, 2019). It has been shown that MITF is the most important transcriptional regulator for driving the numerous signals involved in the expression of genes related to melanogenesis. It regulates the expression of genes with essential roles in cell differentiation, proliferation, and survival. MITF plays an important role in melanocyte development by regulating the expression of tyrosinase (TYR) and tyrosinase related protein 1 (TRP1) and 2 (TRP2). MITF also regulates expression of numerous pigmentation genes to promote melanocyte differentiation, as well as fundamental genes for maintaining cell homeostasis, including genes encoding proteins involved in apoptosis (eg, BCL2) and the cell cycle (eg, CDK2). Intriguingly, many of the molecular pathways important for pigment cell development are also implicated in the formation of melanoma: therefore, the mechanisms controlling the development of pigment cells may provide invaluable insights into the cells' malignant transformation (Hsiao and Fisher, The roles of Microphthalmia Transcription Factor and pigmentation in melanoma. *Arch Biochem Biophys*, 563, 28-34, 2014).

As noted, melanocytes produce and transfer melanin pigments to keratinocytes, where, among other purposes, the pigments help to protect the skin from UV damage. Tyrosinase initiates the melanin biosynthetic pathway, melanogenesis, by oxidizing tyrosine to L-DOPA. MITF stimulates melanogenesis by activating transcription of TYR and other pigmentation genes including TRP1, TRP2 (DCT), PMEL, and MLANA (Yasumoto, et al. Microphthalmia-associated transcription factor as a regulator for melanocyte-specific transcription of the human tyrosinase gene, *Mol Cell Biol* 1994; 14:8058-8070; Du J, et al, MLANA/MART1 and SILV/PMEL17/GP100 are transcriptionally regulated by MITF in melanocytes and melanoma. *Am J Pathol* 2003; 163:333-343). MITF also regulates certain ubiquitously expressed genes that are important for melanocyte survival (e.g., BCL2) and proliferation (e.g., CDK2) (McGill, et al, Bcl2 regulation by the melanocyte master regulator Mitf modulates lineage survival and melanoma cell viability. *Cell* 2002; 109:707-718; Du, et al, Critical role of CDK2 for melanoma growth linked to its melanocyte-specific transcriptional regulation by MITF. *Cancer Cell* 2004; 6:565-576) (Table 1). It is also important to note that MITF target genes are dysregulated in melanoma.

TABLE 1

The master role of MITF in melanocyte and melanoma biology

| | |
|---|---|
| Differentiation | TYR, TRP1, TRP2 (DCT), PMEL, MLANA |
| Cell cycle | CDK2 |
| Survival | BCL2, BCL2A1 |
| Metabolism | PPARGC1A |

Melanocytes endure a large degree of oxidative stress not only due to exogenous insults to the skin, such as UV exposure, but also endogenously because the melanogenesis process itself produces ROS (Denat et al., Melanocytes as instigators and victims of oxidative stress, *J Invest Dermatol*, 134:1512-1518, 2014]. Specifically, recent research has shown melanin inducer α-melanocyte-stimulating hormone (α-MSH) caused ROS generation that was inhibited by the NADPH oxidase inhibitor Diphenyleneiodonium (DPI) in B16 cells (G S Liu et al., Microphthalmia-associated transcription factor modulates expression of NADPH oxidase type 4: a negative regulator of melanogenesis, *Free Radic*

Biol Med, 52 (9): 1835-1842, 2012). Interestingly, it was insensitive to antagonists of other ROS-producing enzyme systems including mitochondrial enzymes, cycloxygenase, and xanthine oxidase. Additionally, these authors reported that α-MSH activated its downstream signal MITF to stimulate NOX4 gene expression. Interesting to note that boosting MITF signaling results in the stimulation of NOX4 which drives ROS generation, thereby increasing melanin synthesis. Such sequence of actions appears to act as an internal feedback mechanism to fine-tune melanin synthesis in response to exogenous challenges such as UV radiation.

In light of the foregoing, it appears that melanocytes need to employ endogenous antioxidant systems to combat ROS, including the thioredoxin and glutathione (GSH) antioxidant systems. The thioredoxin antioxidant system is composed of nicotinamide adenine dinucleotide phosphate (NADPH), thioredoxin reductase 1 (TrxR1), and thioredoxin (Trx). This system works by the transfer of electrons from NADPH to TrxR1, allowing it to reduce protein disulfides on Trx, which can then go on and reduce its own substrates [Holmgren and Lu, Thioredoxin and thioredoxin reductase: current research with special reference to human disease, *Biochem Biophys Res Commun*, 396:120-124, 2010]. Additionally, TrxR1 is known to have elevated expression in the skin after UVR [Casidy et al., A Phase II randomized placebo-controlled trial of oral N-acetylcysteine for protection of melanocytic nevi against UV-induced oxidative stress in vivo. *Cancer Prev Res (Phila)*, 10:36-44, 2017] and is highly upregulated in many cancer types [Thioredoxin reductase as a novel molecular target for cancer therapy, *Cancer Lett*, 236:164-174, 2006]. The Thioredoxin system is one of the major antioxidant systems that can function against oxidative stress, and it is present in all species [Lu and Holmgren, The thioredoxin superfamily in oxidative protein folding, *Antioxidant Redox Signal*, 2014; 21:450-470]. The Trx system contributes to many essential cellular functions, such as gene expression [Chang W H et al., Regulation of thioredoxin gene expression by vitamin A in human airway epithelial cells, *American J Resp Cell Mol.* 2002; 26:627-635], DNA synthesis [Sodeberg O et al., Interleukin-15+ thioredoxin induce DNA synthesis in B-chronic lymphocytic leukemia cells but not in normal B cells, *Leukemia*, 1997; 11:1298-1304], signal transduction [Bai J, et al., Critical roles of thioredoxin in nerve growth factor-mediated signal transduction and neurite outgrowth in PC12 cells, *J. Neurosci*, 2003; 23:503-509], cell growth and apoptosis [Liu H et. al., Activation of apoptosis signal-regulating kinase 1 (ASK1) by tumor necrosis factor receptor-associated factor 2 requires prior dissociation of the ASK1 inhibitor thioredoxin [Nadeau P et al., Disulfide Bond-mediated Multimerization of Ask1 and Its Reduction by Thioredoxin-1 Regulate $H_2O_2$-induced c-Jun $NH_2$-terminal Kinase Activation and Apoptosis, *Mol Cell Biolo*, 2002; 20:2198-2208]. Additionally, it has been shown that reduced Trx suppresses melanin synthesis by reacting with tyrosinase, thus inhibiting tyrosinase activity. In following, it has been reported that TrxR1 activity correlates with different skin phototypes I-VI (Fitzpatrick skin type system), where darker skin has significantly higher enzyme activity compared with very fair skin [Schallreuter K U et al., Thioredoxin reductase. Role in free radical reduction in different hypopigmentation disorders, *Arch Dermatol*, 1987; 123:615-619]. In addition, stable knockdown of TrxR1 has been found to result in a significant decrease in melanin levels and tyrosinase activity in melanocytes [Cassidy P et al., Thioredoxin reductase 1 knockdown disrupts pigment synthesis in melanocytes, *Free Radical Biol. Med.* 2018, 128: S64]. These studies suggested that high levels/activities of TrxR1 are correlated with melanin formation: providing additional information on the roles of cellular antioxidant proteins in melanogenesis. Furthermore, melanocytes exhibited an elevated level of UV-induced DNA damage in the form of 8-oxo-2'-deoxyguanosine after acute UVB treatment. On the other hand, melanocytic TrxR1 has been found to positively regulate melanocyte homeostasis and pigmentation during development and, consequently, protects against UVB-induced DNA damage and oxidative stress [Carpenter et al., Thioredoxin Reductase 1 Modulates Pigmentation and Photobiology of Murine Melanocytes in vivo, *J Invest Dermatol*, 142 (17): 1903-1911.e5, 2022]. The thioredoxin antioxidant system provides a fascinating system to examine redox regulation of physiological processes, and recent data provide compelling firsthand in vivo evidence for the role of an oxidoreductase in positively regulating skin pigmentation, melanocyte homeostasis, and UV-induced oxidative stress [Carpenter et al., Thioredoxin Reductase 1 Modulates Pigmentation and Photobiology of Murine Melanocytes in vivo, *J Invest Dermatol*, 142 (17): 1903-1911.e5, 2022].

It is well known that glutathione (GSH) not only acts as an antioxidant by scavenging free radicals but is also involved in pheomelanin formation. The involvement of GSH in melanogenesis is mediated by two different mechanisms. First, there is a direct interaction between GSH and the active site of tyrosinase, resulting in the activation of tyrosinase activity when the concentrations of GSH is below 3 mM and inhibition at higher GSH concentrations [Jara et al., The role of sulfhydryl compounds in mammalian melanogenesis—the effect of cysteine and glutathione upon tyrosinase and the intermediates of the pathway, *Biochim Biophys Acta*, 967, 296-303, 1988]. Second, the reaction of the GSH thiol group with dopaquinone leads to the formation of a sulphydryl-dopa conjugate and finally to a sulfur-containing pigment, pheomelanin instead of eumelanin [Jara et al., The role of sulfhydryl compounds in mammalian melanogenesis—the effect of cysteine and glutathione upon tyrosinase and the intermediates of the pathway, *Biochim Biophys Acta*, 967, 296-303, 1988; Rorsman at al., Thiols in the melanocyte, *Pigment Cell Res*. 1, 54-60, 1988; Motohashi et al., Inhibitory effects of sulfur-compounds on melanin formation reaction by tyrosinase. *Chem. Pharm. Bull.* 39, 142-145, 1991]. Conversely, del Marmol and colleagues showed that the inhibition of GSH synthesis promoted tyrosinase activity and favored eumelanogenesis in human melanoma cells [del Marmol et al., Glutathione depletion increases tyrosinase activity in human melanoma cells. *J. Invest. Dermatol.* 101, 871-874, 1993]. Therefore, GSH, as an antioxidant with anti-melanogenic properties, has recently become the focus of attention in evaluating its suitability as a skin lightening agent [Lu et al., Modulating skin colour: role of the thioredoxin and glutathione systems in regulating melanogenesis, *Biosci Rep*. 41 (5): BSR20210427, 2021]

In the world of cosmetics and cosmetology, skin beauty starts with healthy skin: skin glow, even tone and radiance are holistic measures that define healthy skin. As mentioned above, skin coloration is primarily regulated by the amount and type of melanin synthesized by the melanocytes [Ito SA, Chemist's view of melanogenesis, *Pigment Cell Res*, 2003; 16:230-236; Kasraee B, Peroxidase-mediated mechanisms are involved in the melanotoxic and melanogenesis-inhibiting effects of chemical agents, *Dermatol*, 2002; 205:329-339]; however, additional and equally contributing factors include (a) the efficiency of the transfer of the melanosomes, hence the melanin, from the melanocytes to the neighboring keratinocytes, a process that occurs with the help of E-Cadherin, an adhesion protein, and (b) the subsequent 3-D spatial distribution and degradation of the transferred melanosomes by the recipient keratinocytes [Hearing V J, Regulating melanosome transfer: who's driving the bus, *Pig Cell Res,* 2007; 20:334-335].

Hyperpigmentation, hypopigmentation, and other pigmentation disorders are quite common and can arise from several causes including diet, skin trauma, environmental factors, medications, disease, and the like. Additionally, post inflammatory hyper-pigmentation is found to occur following laser and similar therapies. Common pigmentation disorders, which include melasma (dark patches experienced in pregnancy) and liver spots (which often develop with age), and may arise as a side effect of birth control pills, and/or as a persistent result of acne, burns, bites and other skin injuries, and vitiligo. Similarly, freckles, chloasma and pigmentary deposits after sun exposure tend to occur or increase or intensify or become less likely to disappear or lighten with increasing age. Consequently, such age-related issues skin coloration issues are one of the more disconcerting and/or common problems of skin care for persons of middle to advanced age.

To address such pigmentation disorders, various preparations have been formulated, especially for use in the treatment of age spots and freckles or to obtain even-toning effects. Such treatments are not, however, limited to use in treating disorders but are also used in some cultures/markets merely for the purpose of changing or modifying one's natural skin color. Such treatments are typically referred to by a few different terminologies including "skin lightener", "skin whitener", "skin even-toner" and "skin brightener". The specific terminology used is oftentimes a matter of regulatory controls; rather than one of performance or application. For example. "skin whitening" terminology is very commonly used in Asia whereas such terminology is not allowed under US Food and Drug Administration regulations. Other terminologies are commonly used as well, including, melanin inhibitory agents, depigmenting agents, tyrosinase inhibitors (tyrosinase being the key enzyme responsible for melanin synthesis), etc. Whatever terminology is employed, the general premise is that they all relate to a reduction in the formation and/or rate of formation of melanin. In this specification, the terms "skin lightener", "skin brightener" and "even-toner" will be used as they are physiologically more relevant.

Several agents and methods for skin lightening have been developed and put on the market. Such methods include the oral administration of large doses of Vitamin C, the parenteral administration of glutathione, and the topical application of Vitamin C and/or cysteine. Vitamin C, however, has stability issues, especially in water-based formulations, resulting in color and odor changes. Thiol compounds such as glutathione and cysteine are weak and/or manifest generally poor depigmentation performance properties.

Perhaps the most employed skin lightening agent has been hydroquinone and its derivatives. However, these compounds, while effective, have serious, detrimental side effects. Even at concentrations below 2%, hydroquinone is both imitating and cytotoxic to the melanocytes. With the growing concern as to their safety, hydroquinone and its derivatives are largely being phased out of use or banned altogether in topical applications. Similar problems have been experienced with Kojic acid depigmentation agents as well.

A wide-range of polyphenols present in plant extracts have also been used for skin lightening/even-toning purposes. Melanin inhibitory activity of natural polyphenols, such as, anthraquinones [Jones et al., Modulation of melanogenesis by aloeosin: a competitive inhibitor of tyrosinase, *Pigment Cell Research,* 15, 335-340, 2002], arylbenzofurans [Lee et al., Mulberoside F isolated from the leaves from the leaves of Murus alba inhibits melanin biosynthesis, *Bio Pham Bull,* 25, 1045-1048, 2002], chalcones [Nerya et al., Chalcones as potent tyrosinase inhibitors: the effect of hydroxyl positions and numbers, *Phytochem,* 65, 1389-1395, 2004], coumarins [Masamoto et al., Inhibitory effects of esculetin on melanin biosynthesis. *Biol Pharm Bull,* 27, 422-425, 2004], flavonoids [Yokoto et al., The inhibitory effect of glabridin from licorice extracts on melanogenesis and inflammation, *Pigment Cell Research,* 11, 355-361, 1998; No et. al., Inhibition of tyrosinase by green tea components, *Pharmacol Letters,* 65, 241-246, 1999; Nerya et al., Glabrene and Isoliquiritigenin as tyrosinase inhibitors from Licorice roots, *J Agr Food Chem,* 51, 1201-1207, 2003; Kubo et al., Flavonols from Heterotheca inuloides: Tyrosinase inhibitory activity and structural criteria, *Bioorganic & Medicinal Chemistry,* 8, 1749-1755, 2000], Stilbenes [Shin et. al., Oxyresveratrol as the potent inhibitor on dopa oxidase activity on mushroom tyrosinase, *Biochem Biophys Res Commun,* 243, 801-803, 1998; Kim et al., Oxyresveratrol and hydroxystilbene compounds, *J Biol Chem,* 277, 16340-16344, 2002], and low molecular weight tannins [Chaudhuri et al., Inhibitory effects of Phyllanthus emblica tannins on melanin synthesis, *Cosmetics & Toiletries,* 122 (2). 73-80, 2007] have been reported. Exemplary patents that describe the use of natural and synthetic phenolic compounds as skin lighteners include U.S. Pat. No. 6,649,150-Chaudhuri et al.; U.S. Pat. No. 6,969,509-Chaudhuri et al.; U.S. Pat. No. 5,670,154-Hara et al.; and U.S. Pat. No. 5,880,314-Shinomiya et. al.

One class of polyphenolic compounds that has received a lot of attention, at least in the patent literature, is that based on substituted resorcinols and their derivatives. Early applications, including U.S. Pat. No. 4,959,393—Torihara et. al., employed n-alkyl substituted resorcinols, especially those based on $C_2$ to $C_{12}$ n-alkyl substituted resorcinol. Subsequent applications, including JP 5-04905—Hamazaki et. al. and WO 2006/049184—Fukunishi et. al., focused on compositions containing 4-alkylresorcinol derivatives including, straight chain and branched, $C_2$ to $C_{12}$ n-alkyl substituted resorcinols and their salts. Others employed such 4-alkylresorcinols, especially n-butylresorcinol, in combination with certain branched polymers, e.g., acrylic acid-alkyl methacrylate, JP 2001-010925—Seto et. al. Chaudhuri has employed highly purified 4-hexylresorcinol (99% plus) as a skin lightening agent and has patented this innovation (EP 2,152,685). This hexylresorcinol is commercially available from Sytheon as Synovea® HR which can be used alone or combination with other skin lightening ingredients, such as Niacinamide (EP 2,152,685) or Acetyl Zingerone (Synoxyl®) AZ: US 510,838,241).

Though early developmental activities relative to the resorcinols seemed to focus on the simple alkyl substituted resorcinols, much greater focus has more recently been directed to the more complex, hydrocarbyl and/or hetero moiety substituted resorcinols. Hetero-substituted resorcinols include the thio, thiane (especially dithiane), amide, amine, keto and carboxylic substituted resorcinols as shown in U.S. Pat. No. 5,468,472—LaGrange et. al.; U.S. Pat. No. 6,875,425—Harichian et. al., U.S. Pat. No. 6,852,310—Harichian et. al.; and JP 1125563—Sakai. Perhaps the greatest attention has focused on the more complex hydrocarbyl substituted resorcinols, specifically, the cycloalkyl resocinols and substituted derivatives thereof. Such skin lightening agents are more fully described in, e.g., US 2006/0257340—Nair; U.S. Pat. No. 6,878,381—Collington; U.S. Pat. No. 6,933,319—Browning et. al.; U.S. Pat. No. 6,852,747—Bradley et. al.; U.S. Pat. No. 6,828,460—Browning et. al.; U.S. Pat. No. 6,797,731-Bradley et. al.; U.S. Pat. No. 6,590,105—Bradley et. al.; U.S. Pat. No. 6,541,473—Bradley et. al.; and U.S. Pat. No. 6,132,740—Hu.

Despite the significant focus on substituted resorcinols and their derivatives, they too are not without their problems. For example, despite their relatively good skin lightening capabilities, they tend to suffer from stability issues, particularly color stability. In following, efforts have been undertaken to improve their stability by the incorporation of various additives including metal oxides (U.S. Pat. No. 6,863,897—Love et. al.) and terpenoids (U.S. Pat. No. 6,858,217—Kerschner et. al.); however, their success has been limited.

Hence, despite all the advances, there remains a need for skin lightening agents that do not suffer from instability, especially oxidative instability that affects the color and efficacy of the skin lightening composition as well as the cosmetic/treatment formulation into which the skin lightening agents are incorporated.

Similarly, there remains a need for skin lightening agents that do not possess or raise concerns relative to skin irritancy and sensitization, or other possible skin or health consequences.

In general, there remains a need for additional skin lightening agents, especially ones of high efficacy. Most especially, there remains a need for skin lightening agents that are highly efficacious, stable, and non-irritating.

Furthermore, there is also a need for skin lightening agents that are multitargeted and compatible with and, most preferably, work synergistically with other skin lightening agents, especially in ways that enable the use of less and less skin lightening actives without compromising efficacy.

Finally, there remains a need for skin lightening compositions that achieve any or all the foregoing objectives and are easy to use with highly efficacious results.

SUMMARY

According to the present teaching there are provided active agents and compositions that are multitargeted skin lightening and even-toning agents and compositions having antioxidant activity which work by reducing oxidase activity.

According to the first aspect of the present teaching there are provided novel compounds, namely, zinc di-(di-n-butyryl lysinate), also referred to as Bis (N2, N6-di-n-butyryl-Lysine) zinc salt (2:1)], as depicted in Structure 1

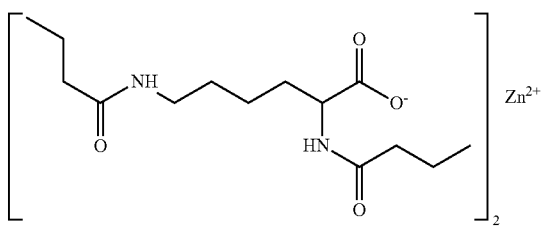

Structure 1 and zinc di-(di-isobutyryl lysinate), also referred to as Bis (N2, N6-di-isobutyryl-Lysine) zinc salt (2:1)], as depicted in Structure 2

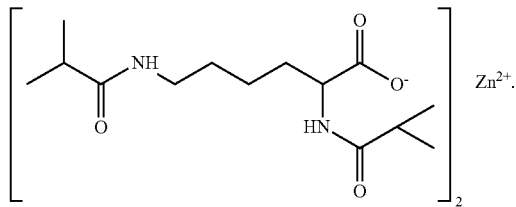

Structure 2

According to a second aspect of the present teaching there are provided novel topical compositions comprising (I) either zinc di-(di-n-butyryl lysinate), zinc di-(di-isobutyryl lysinate) or a mixture of the two (collectively the "zinc dibutyryl lysinate component"), preferably zinc di-(di-n-butyryl lysinate), (ii) optionally, though preferably, a skin lightening agent that is not (i), and (iii) a dermatologically acceptable carrier. Preferably, these compositions are topically applied skin lightening/brightening/even-toning compositions or, depending upon the selection of the dermatologically acceptable carrier, a topical composition which has a different primary purpose in addition to the ability to lighten, brighten and/or move evenly tone skin, particularly skin coloration. With respect to the former, while these formulations are effective as skin lightening/brightening/even-toning compositions, they are also suitably employed as preventative compositions to be applied routinely, especially daily, for preventing the formation of sun-induced, laser and other therapy-induced or scar-induced hyper-pigmented spots as well as that resulting from other factors including diet and/or pharmaceutical agents and/or physiological changes. With respect to the latter, the dermatologically acceptable carrier may be a formulated product having a primary purpose other than skin lightening/brightening/even-toning, including, but not limited to cosmetics, moisturizers, sunscreens, sunburn treatments, anti-aging products and the like as well as topical pharmaceutical products intended to address acne, eczema, psoriasis, and the like, whereby the presence of the zinc dibutyryl lysinate component, has the added benefit/property of skin lightening/brightening/even-toning.

The compositions, preferably skin lightening compositions, of the present teaching will typically comprise from about 0.05 to about 20 wt. %, preferably from about 0.1 to about 10 wt. %, of the zinc dibutyryl lysinate component, preferably zinc di-(di-n-butyryl lysinate), based on the total weight of the formulation. Exemplary preferred compositions contain from about 0.5 to about 5 wt. %, especially from about 0.5 to 2 wt. %, based on the total weight of the composition. As noted, the zinc dibutyryl lysinate component may be used alone or in combination with one or more other skin lightening, even-toning and/or skin brightening agents, collectively referred to as the "second skin lightening agent." When the second skin lightening is present, it will be present in amounts typical for that agent, generally on the order of from about 0.01 to about 20 wt. %, preferably from about 0.5 to about 10 wt. %, most preferably from about 0.1 to about 5 wt. %. Where synergy is found, though the aforementioned ranges still apply, one is able to reduce the amount of either or both of the skin lightening agents to achieve the same desired result. Owing to the reduced issues with the zinc dibutyryl lysinate component, particularly, zinc di-(di-n-butyryl lysinate), it is preferred to reduce the amount of the second skin lightening agent, which may be reduced by up to 50% or more. Most preferably, where synergy is present, the second skin lightening agent is most preferably present in an amount of from about 0.5 to about 2.5 wt %. Furthermore, when the second skin lightening agent is used, it is preferred that the weight ratio of the zinc dibutyryl lysinate component, to the second skin lightening agent(s) is from 10:1 to 1:10, preferably 5:1 to 1:5, most preferably 2:1 to 1:2. Of course the specific ratio also depends, in part, upon the molecular weight(s) of the other skin lightening agent(s).

The zinc di-(butyryl lysinate) component, especially the zinc di-(di-n-butyryl lysinate), alone or in combination with one or more additional skin lightening agents, is incorporated into conventional dermatologically acceptable carriers for application/delivery to the subject. Such carriers may be dedicated carriers for the skin lightening agents or may be formulated products themselves, e.g., cosmetics, sunscreens, moisturizers and the like. Whether a formulated product or a dedicated carrier, the skin lightening compositions of the present teaching may optionally include an effective amount of one or more skin protective and/or treatment ingredients such as sunscreens, antioxidants, vitamins, anti-inflammatory agents, moisturizers, emollients, humectants, amphoteric surfactants, alcohols (more specifically, ethanol), and the like, and mixtures thereof, in their conventional amounts.

Finally, according to a third aspect of the present teaching there are provided methods for lightening skin coloration, creating a more even tone of skin coloration and/or preventing skin discoloration and/or undesirable coloration which method comprises applying the aforementioned composition to the skin. Specifically, the skin lightening compositions of the present invention are applied topically and may take the form of a cream, lotion, spray, solutions, ointment, gel, or other any other topically applicable form. The quantity applied is that which provides a thin film of the composition to the skin to which it is applied: like the application of moisturizers and sunscreen products. Typically, they are applied at least once a day to those areas of the skin for which even toning and/or skin lightening is desired until the desired skin tone or lightening is achieved. Preferably, especially where it is used as a preventative or mitigator of the manifestation of skin coloration or discoloration, the skin lightening composition of the present teaching is applied daily, particularly to those areas of the skin that are prone to undesired coloration or discoloration and/or exposed to the cause of the undesired coloration or discoloration. Like a sunscreen, it is preferred to reapply the composition of the present teaching when long duration sun exposure is ongoing and/or there is concern that the composition may have washed off, e.g., due to perspiration, swimming, etc.

DETAIL DESCRIPTION

All patents, patent publications, and technical articles referenced herein are hereby incorporated in their entirety.

As used herein and in the appended claims, the phrase "substantially free of" means that the recited compound or component, if present, is present in an insufficient amount to manifest any skin irritation or sensitization following topical application: in such regard, it will be as if the same formulation were essentially, if not completely, free of the recited compound or component.

As used herein the term "dermatologically acceptable" means that the recited composition or components thereof are suitable for use in contact with human skin without undue toxicity, incompatibility, instability, irritability, allergic response, and the like.

As used herein the term "topical" or "topically" refers to the application or delivery of the identified material or composition onto the surface of the skin or a portion thereof.

As used herein the term "safe and effective amount" means an amount of a compound or composition sufficient to bring about the desired result or effect without undue toxicity, sensitization, or allergic response.

As used herein the term "post-inflammatory hyperpigmentation" refers to the changes in melanin content as a response to an inflammatory event (e.g., acne, scratch, laser therapy, insect sting or bite, sunburn, etc.).

Finally, as noted above, the term "zinc dibutyryl lysinate component" refers to zinc di-(di-n-butyryl lysinate), zinc di-(di-isobutyryl lysinate) and mixtures of the two. Reference to zinc di-(di-n-butyryl lysinate) or zinc di-(di-isobutyryl lysinate) means the specific compounds themselves.

According to the present teaching there is provided an active agent and compositions containing the same that are multitargeted skin lightening and even toning agents and compositions having antioxidant activity which work by reducing oxidase activity as summarized below in Table 2.

TABLE 2

| Cellular Antioxidants Involved in Melanogenesis | | |
| --- | --- | --- |
| Antioxidants | Role in the Antioxidant System | Role in Melanogenesis |
| Thioredoxin (Trx) | Acts as an antioxidant by reducing other proteins through thiol-disulfide interchange reactions | Suppress melanogenesis by reacting with the binuclear copper center of tyrosinase |
| Thioredoxin reductase (TrxR) | Catalyzes the reduction of oxidized Trx using NADPH | Inhibiting TrxR activity reduces melanogenesis |
| Glutathione (GSH) | Protects cells from oxidative stress & maintains the cellular level of GSH at the normal range | Competes with tyrosine for tyrosinase active site |
| GSH reductase | Converts Oxidized form of GSSG back to its reduced form GSH | Inhibits depletion of GSH, hence suppression of melanogenesis |

[Y Lu et al., Modulating skin colour: role of the thioredoxin and glutathione systems in regulating melanogenesis, *Bioscience Reports*, 2021, 41(5): BSR20210427]

Specifically, according to the first aspect of the present teaching there are provided novel compounds, namely, zinc di-(di-n-butyryl lysinate), also referred to as Bis (N2, N6-di-n-butyryl-Lysine) zinc salt (2:1)], as depicted in Structure 1

Structure 1

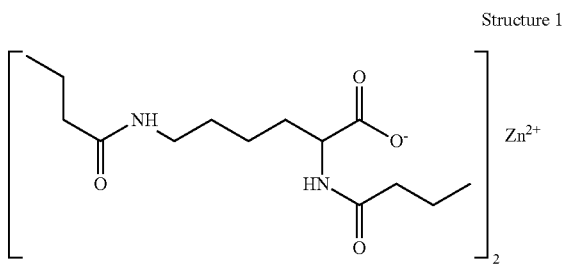

and zinc di-(di-isobutyryl lysinate), also referred to as Bis (N2, N6-di-isobutyryl-Lysine) zinc salt (2:1)], as depicted in Structure 2

Structure 2

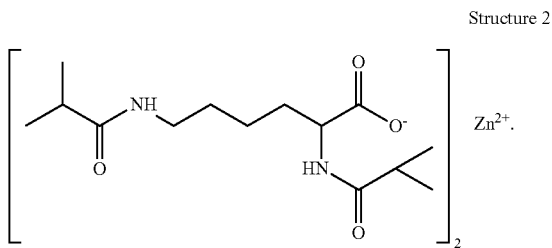

According to a second aspect of the present teaching there are provided novel topical compositions comprising (i) either zinc di-(di-n-butyryl lysinate), zinc di-(di-isobutyryl lysinate) or a mixture of the two (collectively the "zinc dibutyryl lysinate component"), preferably zinc di-(di-n-butyryl lysinate), (ii) optionally, though preferably, a skin lightening agent that is not (i), and (iii) a dermatologically acceptable carrier. Preferably, these compositions are topically applied skin lightening/brightening/even-toning compositions or, depending upon the selection of the dermatologically acceptable carrier, a topical composition which has a different primary purpose in addition to the ability to lighten, brighten and/or move evenly tone skin, particularly skin coloration. With respect to the former, while these formulations are effective as skin lightening/brightening/even-toning compositions, they are also suitably employed as preventative compositions to be applied routinely, especially daily, for preventing the formation of sun-induced, laser and other therapy-induced or scar-induced hyper-pigmented spots as well as that resulting from other factors including diet and/or pharmaceutical agents and/or physiological changes. With respect to the latter, the dermatologically acceptable carrier may be a formulated product having a primary purpose other than skin lightening/brightening/even-toning, including, but not limited to cosmetics, moisturizers, sunscreens, sunburn treatments, anti-aging products and the like as well as topical pharmaceutical products intended to address acne, eczema, psoriasis, and the like, whereby the presence of the zinc dibutyryl lysinate component, has the added benefit/property of skin lightening/brightening/even-toning.

Other skin lightening, even-toning and/or skin brightening active agents are well known and widely available. Generally speaking, any of the known skin lightening agents may be used in combination with the zinc dibutyryl lysinate component. Exemplary, suitable skin lightening agents are discussed in the Background above as well as in the patent citations mentioned herein. Obviously, it is not possible to list all known skin lightening agents, however, examples of suitable skin lightening, even-toning and/or skin brightening agents that may be used in combination with zinc the dibutyryl lysinate component include, but are not limited to, *Phyllanthus emblica* fruit extract, *Terminalia chebula* fruit extract, bearberry extract, mulberry extract, licorice extract, propolis extract, aceroal cherry fermentate, cucumber extract, Green tea poly phenols, Grape seed extract, Pine bark polyphenols, resveratrol, oxyresveratrol, stilbenes, coumarins, flavonoids, niacinamide, anthraquinones, xanthones, lignans, glabridin, curcumine, dihydrocurcumine, tetrahydrocurcumine, epigallocatechin-3-gallate, hydroxy benzoic acids or their derivatives, tomato glycolipids, perilla plant, ligusticum lucidum extract, bakuchiol, ascorbic acid and its derivatives including ascorbyl glucoside, ethyl ascorbic acid, and tetrahexyldecyl ascorbate, Kojic Acid, Alpha-arbutin, Glutathione, Azelaic acid, Glycolic acid, Linoleic acid, Coffee berry extract, Hydroquinone, Pancratium Maritimum extract, resveratrol, bisabolol, Mequinol, 4-hydroxyanisole, hydroquinone monomethyl ether, N-acetyl-4-S-cysteaminylphenol, Alpha tocopherol (Vitamin E), Broussonetica kazwoki, B. Papyrifera, Cornus officinalis, Rhus javanica, Pinus densiflora, orchid extract, aloe vera extract, Pycnogenol, Cinnamic acid, gallic acid, ellagic acid, Umbelliferone, Boswellia, N-Acetyl Glucosamine, retinoids, esp, tretinoin, Ferulic acid, Quercetin, Tranexamic acid, thiamidol, soy, and alkyl resorcinols, especially hexylresorcinol, butylresorcinol and phenylethyl resorcinol, and combinations of any two or more of the foregoing. While certain polyphenol skin lightening agents such as the substituted resorcinols and their derivatives are especially desirable and beneficial, it is to be appreciated that many of the aforementioned resorcinols have considerable levels of impurities and other agents therein, particularly high or significant resorcinol contents. In following, it is preferred that the resorcinol skin lightening/even toning agents be of relatively high purity and/or have low resorcinol content; otherwise, much of the benefit of the present invention may be compromised.

Other suitable skin lightening agents include the sugar amines, which are also known as amino sugars, and are to be employed in a safe and effective amount. The sugar amine compounds useful in the present invention are described in U.S. Pat. No. 6,159,485. Sugar amines can be synthetic or natural in origin and can be used as pure compounds or mixtures of compounds (e.g., extracts from natural sources or mixtures of synthetic materials). For example, glucosamine is generally found in many shellfish and can also be derived from fungal sources. As used herein, the term "sugar amine" is employed in a general sense and includes the sugar amines themselves, their isomers and tautomers, as well as their salts (e.g., HCl salt). Sugar amines are commercially available from, e.g., Sigma Chemical Co. Exemplary suitable sugar amines include glucosamine, N-acetyl glucosamine, glucosamine sulfate, mannosamine. N-acetyl mannosamine, galactosamine, N-acetyl galactosamine, their isomers (e.g., stereoisomers), and their salts (e.g., HCl salt). Preferred sugar amines are glucosamine, particularly D-glucosamine and N-acetyl glucosamine, particularly N-acetyl-D-glucosamine.

Yet another group of skin lightening agents are the N-acyl amino acid compounds, including, but not limited to, N-acyl phenylalanine, N-acyl tyrosine, their isomers, including their D and L isomers, salts, derivatives, and mixtures thereof. An example of a suitable N-acyl amino acid is N-undecylenoyl-L-phenylalanine is commercially available under the tradename Sepiwhite™ from Seppic (France).

The skin lightening compositions of the present teaching will typically comprise from about 0.05 to about 10 wt. %, preferably from about 0.1 to about 10 wt. %, of the zinc dibutyryl lysinate component, particularly zinc di-(di-n-butyryl lysinate), based on the total weight of the formulation. Exemplary preferred compositions contain from about 0.5 to about 5 wt. %, especially from about 0.5 to 2 wt. %, of the zinc dibutyryl lysinate component based on the total weight of the composition. As noted, the zinc dibutyryl lysinate component may be used alone or in combination with one or more other skin lightening, even-toning and/or skin brightening agents, collectively referred to as the "second skin lightening agent." When present, the second skin lightening agent will be present in amounts typical for that agent, generally on the order of from about 0.01 to about 20 wt. %, preferably from about 0.5 to about 10 wt. %, most preferably from about 0.1 to about 5 wt. %. Where synergy is found, though the aforementioned ranges still apply, one is able to reduce the amount of either or both of the skin lightening agents to achieve the same desired result. Owing to the reduced issues with the zinc dibutyryl lysinate component, particularly zinc di-(di-n-butyryl lysinate), it is preferred to reduce the amount of the second skin lightening agent, which may be reduced by up to 50% or more. Most preferably, where synergy is present, the second skin lightening agent is most preferably present in an amount of from about 0.5 to about 2.5 wt %. Furthermore, when the second skin lightening agent is used, it is preferred that the weight ratio of the zinc dibutyryl lysinate component to the second skin lightening agent is from 10:1 to 1:10, preferably 5:1 to 1:5, most preferably 2:1 to 1:2. Of course the specific ratio also depends, in part, upon the molecular weight(s) of the second skin lightening agent(s).

The zinc dibutyryl lysinate component, with or without the second skin lightening agent(s), is delivered or applied to the skin in a suitable dermatologically acceptable carrier. Such carriers are well known and widely available. Preferably, the carriers are those carriers and excipients that are suitable for long term and repeated application to the skin without manifesting sensitization, irritation or inflammation. The specific carrier material will depend upon the delivery method itself. For example, the skin lightening/even-toning/skin brightening compositions may be in the form of lotions, creams, gels, foams, emulsions, dispersions, sprays, liposomes, coacervates, etc. Each composition will typically include any of the known topical excipients and agents necessary for achieving the particular form of the final composition. Suitable excipients include, e.g., mineral oils, silicone oils and emulsifying agents. In its most simple of embodiments, the carrier may be water, alcohol or water/alcohol combinations, or other solvent(s) or solvent systems in which the aforementioned actives may be, e.g., soluble, dispersed, emulsified, etc. Preferably, though, the skin lightening compositions will include excipients and the like that create a substantially stable, homogenous skin lightening/even-toning composition and/or provide body and viscosity to the skin lightening/even-toning composition so that the actives do not merely run off the skin once applied. Typically, the carrier will comprise from about 30 to more than 99 wt. %, preferably from 40 to 99 wt. %, of the skin lightening composition.

Generally speaking, any known carrier or base composition employed in traditional cosmetic and/or dermatological applications/compositions can be used in the practice of the present teaching. Similarly, those skilled in the art will readily recognize and appreciate what carriers may be employed considering the intended form and/or delivery method for the skin lightening/even-toning compositions. Suitable carriers and carrier compositions are described at length in, for example, Gonzalez et. al.—U.S. Pat. No. 7,186,404; Aust et. al.—U.S. Pat. No. 7,175,834; Roseaver et. al.—U.S. Pat. No. 7,172,754; Simoulidis et. al. —U.S. Pat. No. 7,175,835; Mongiat et. al.—U.S. Pat. No. 7,101,536; Maniscalco—U.S. Pat. No. 7,078,022; Forestier et. al. U.S. Pat. Nos. 5,175,340, 5,567,418, 5,538,716, and 5,951,968; Deflandre et. al.—U.S. Pat. No. 5,670,140; Chaudhuri—U.S. Pat. Nos. 7,150,876, 6,831,191, 6,602,515, 7,166,273, 6,936,735, 6,831,191, and 6,699,463; Chaudhuri et. al.—U.S. Pat. Nos. 6,165,450 and 7,150,876; Bonda et. al. U.S. Pat. No. 6,962,692; Rodan et. al.—U.S. Pat. No. 9,144,434, Wang et. al. U.S. Pat. No. 5,830,441 and Auspitz et. al.—US 2007/0110685 A.

In addition to or instead of the second skin lightening agent, the skin lightening compositions of the present teaching may, and preferably do, include one or more additional ingredients, including ingredients that are, themselves, skin active ingredients and have an impact or effect on the skin. Exemplary supplemental skin active ingredients include antioxidants, sunscreen actives, vitamins, anti-inflammatory agents, moisturizers, emollients, humectants, anti-acne ingredients, and the like. Such supplemental active ingredients include, but are not limited to bakuchiuol, isosorbide dicaprylate, terminalia chebula fruit extract, ethyl linoleate, isosorbide dilinoleate, isosorbide disunflowerseedate and mixtures thereof. Alternatively, or in addition thereto, these compositions also include other ingredients that have no or little bearing upon the intended end-use or application of the treatment aspect of these compositions, but aid in the preparation and/or longevity/stability of these compositions as well as the aesthetic aspects thereof. Exemplary inactive ingredients include solubilizers, surfactants, stabilizers, thickeners, preservatives, buffers, dyes, perfumes, scents, opacifiers, colorants, etc. Each of these is typically present, when present, in conventional amounts for those ingredients. It is not necessary to identify all of the possible specific active and non-active ingredients and additives that can be incorporated into the compositions of the present teaching as they are well known and widely available and, in any event, any attempt to do so would run on for page after page.

Another type of ingredient that may be used, one which is not really a skin active agent nor an inactive ingredient, are penetrants. Specifically, additives that, when applied to the skin, have a direct effect on the permeability of the skin barrier: increasing the speed with which and/or the amount by which certain other compounds penetrate the skin layers. Exemplary organic penetration enhancers include dimethyl sulfoxide; isopropyl myristate; decyl, undecyl or dodecyl alcohol; propylene glycol; polyethylene glycol; $C_{9-11}$, $C_{12-13}$ or $C_{12-15}$ fatty alcohols; azone; alkyl pyrrolidones; diethoxy glycol (Transcutol); lecithin; etc. Surfactants can also be used as penetration enhancers. Again, each is employed in conventional amounts for such ingredients.

Alternatively, rather than specifically formulate a composition based upon the zinc dibutyryl lysinate component, one may simply add the zinc dibutyryl lysinate component, preferably the zinc di-(di-n-butyryl lysinate), solubilized in solubilizer(s)/-solvent, to existing product formulations and commercial products. For example, the zinc dibutyryl lysinate component may be added to existing cosmetics, sunscreens, moisturizers, skin serums, anti-aging compositions, acne treatments, general skin care products, rejuvenation products, topical pharmaceutical products, and the like, or into base compositions employed in the manufacture of the foregoing.

The final form of the skin lightening compositions of the present teaching and their method of manufacture depends, in part, upon the mode of administration as well as the other ingredients to be incorporated into said compositions or the composition into which the zinc dibutyryl lysinate component is to be incorporated. Accordingly, these compositions may be in the form of solutions, suspensions, emulsions, microcapsules, microcapsules containing liquids, powders, creams, lotions, gels, sustained-release formulations, aerosols, sprays, and the like. In following, the compositions may be prepared by any method known in the art for cosmetic and/or dermatological/topical preparations. Such methods include, conventional mixing, agitation, dissolving, granulating, dragee-making, levigating, emulsifying, suspending, encapsulating, homogenization, etc. All of such options and methods are conventional in the art. Additionally, during the preparation, it may be desirable to add known pH adjusters in order to maintain a proper pH of the composition for topical application, especially if basic ingredients are to be employed. Generally, the pH should be on the neutral to slightly acidic side, perhaps as low as pH 4. Preferably, though, the pH will be in the range of from about 5 to about 7, preferably from about 5 to 6.5.

The skin lightening/even toning compositions of the present invention are applied as either a preventative measure to prevent or inhibit skin darkening or as a treatment to address pre-existing skin darkening and/or uneven toning and/or to simply add a brightening to the skin. In the former, the skin lightening/even toning compositions are applied to areas of the skin that are prone to skin darkening such as those exposed to sunlight, in the case of sun-induced hyperpigmentation, including melasma; that are prone to acne and other types of inflammation or skin damage or that are anticipated to undergo a treatment that is associated with inflammation, e.g., laser therapy, where post-inflammatory hyperpigmentation is likely to arise: as well as to areas of the skin where hyperpigmentation has already been reduced and it is desired to maintain a certain skin color and/or tone. Preferably, the skin lightening/even toning composition is applied to skin for which the individual desires a lighter color and/or a more even tone or brightness, especially skin which has developed hyperpigmentation and/or a blotchy or uneven coloration. For example, at one extreme, one may desire to lighten the whole of their skin in which case the composition is applied all over. Alternatively, one may only be concerned with certain areas of the skin in which case one would apply the composition to just those areas of the skin that, e.g., due to long term sun and UV exposure, acne, etc., are darker than the rest of the body. Indeed, vanity may prompt some individuals to use skin lightening and even toning to reduce the appearance of tan lines, freckles, and the like. More importantly, though, the present method is directed to the lightening and even toning of spots and/or select areas of the skin where hyperpigmentation and/or uneven or blotch skin coloration has developed, most often because of or associated with physical and/or physiological events including trauma, inflammation, laser therapy, age, sun exposure, diet, drug or pharmaceutical treatment, pregnancy, etc. Most preferably, and beneficially, particularly from a psychological perspective, the present method is especially directed to the treatment of hyperpigmentation and uneven or blotchy skin coloration arising from trauma, inflammation, laser therapy, diet, drug or pharmaceutical treatment, pregnancy, and other biological conditions or diseases and/or their treatment, other than typical skin aging, in order to enable those stricken with the hyperpigmentation and/or uneven or blotchy skin coloration to avoid the stigma and self-consciousness associated with those conditions. In this respect, age spots and sunspots arising from long-term sun exposure are the norm for aging adults; however, for children, teens and young adults who suffer/suffered from acne, eczema, vitiligo, melisma, etc., the appearance of such hyperpigmentation and/or uneven or blotchy toning is much more traumatic and, even if the unevenness, as in vitiligo, cannot be eliminated in total, it can be muted: any change is seen, particularly from a personal or psychological perspective, as a positive change.

The duration and frequency of application varies, as noted above. Generally speaking, the composition is applied until the desired skin lightening and/or even toning effect is attained. Where the composition is applied as a preventative measure, it will be applied for the duration of the circumstances giving rise to the potential for hyperpigmentation, especially where post-inflammatory hyperpigmentation is of concern. Similarly, once the desired level of skin lightening and/or even toning is achieved, it may be desirable to apply a lesser amount of the skin lightening composition and/or apply it less frequently, to maintain the given skin color, tone and/or brightness. Alternatively, one may apply it daily as a matter of routine in order to maintain a given skin appearance and brightness, as well as even tone.

The amount of the skin lightening/even toning composition that is to be applied to the skin depends upon the form of the skin lightening/even toning composition and its mode of application. Generally speaking, the amount to be applied is that which is sufficient to provide a thin film of the composition to the treated skin. Typically, a small quantity of the composition, for example from 0.1 to 5 ml, is applied to the skin from a suitable container or applicator and spread over and/or rubbed into the skin using the hands or fingers or a suitable device.

The skin lightening compositions are preferably applied at least once daily, more preferably at least twice daily, to the skin generally or to those areas of the skin for which skin lightening and/or even toning is sought until the desired improvement in skin appearance is attained or becomes apparent. This time frame will vary markedly depending upon the extent of lightening and/or toning desired, the darkness of the skin and/or uneven toning of the skin to begin with, the frequency of application, the activity level of the individual and whether the composition is washed or worn away during such activities, as well as the concentration of the skin lightening ingredients, most especially the zinc dibutyryl lysinate component, in the composition and the presence of other ingredients which may boost or inhibit or delay the skin lightening effect of the zinc dibutyryl lysinate component. More preferably, especially for those compositions also containing sunscreen actives, particularly where one is intending to prevent or mitigate hyperpigmentation from UV exposure, the skin lightening/even toning composition should be applied before sun exposure, preferably at least 15 minutes before, and reapplied at least every 2 hours or more frequently, especially if the individual engages in activities/actions that may cause the sunscreen containing skin lightening composition to wear or wipe off, e.g., swimming; washing dishes, windows, etc.; washing hands and/or face; contact sports activities; activities that promote substantial sweating; etc.: all actions/events that cause the premature wearing off or loss of the sunscreen containing composition.

From a duration of application standpoint, typical application periods will extend from 7 days to 6 months or more. However, given the other benefits of the zinc dibutyryl lysinate component, particularly zinc di-(di-n-butyryl lysinate), it may be desirable to continue the application of these compositions as a daily ritual, even after the desired skin lightening and/or even toning effect is achieved, to improve overall skin health and/or to counter the effects of natural skin aging and, more importantly, the detrimental effects of sun exposure and air pollutants. In this regard, a user may adopt a routine of application of a skin lightening composition or other skin care product where the zinc dibutyryl lysinate component, especially zinc di-(di-n-butyryl lysinate), is the key or a key active ingredient to effect the desired skin lightening and/or even toning until the desired effect is attained followed by the use of a daily moisturizer, sunscreen and/or cosmetic composition that also contains the zinc dibutyryl lysinate component, especially zinc di-(di-n-butyryl lysinate), as a constant preventative and therapeutic treatment.

EXAMPLES

Example 1: Preparation Di-n-butyryl Lysine

In tetrahydrofuran and distilled water, L-Lysine HCl (1 mole) and butyric anhydride (2.2 moles) or butyric acid chloride (2.2 moles) were added and stirred for 12 to 16 hours at 30±5° C. Then sodium carbonate was added to the reaction mixture and stirred for another 12 to 16 hours at 30±5° C. Following that, sodium chloride and hydrochloric acid were added and the mixture stirred for 30 min following which the aqueous layer was allowed to separate and was then separated. The remaining organic layer was subjected to distillation under vacuum at <40° C. The crude product was further purified by column chromatography. The purified product was characterized to be di-n-butyryl lysine by spectroscopic methods.

Example 2: Preparation Di-isobutyryl Lysine

Di-isobutyryl lysinate is prepared according to the same procedure as set forth in Example 1 with the exception that isobutyric anhydride (2.2 moles) or isobutyric acid chloride (2.2 moles) is substituted for the butyric anhydride or butyric acid chloride, respectively.

Example 3: Preparation of Zinc Di-(di-n-butyryl Lysinate)

Di-n-butyryl lysine (2 moles) from Example 1 was mixed with methanol and zinc hydroxide (1.1 moles) and heated to 65° C. and the mixture maintained at that temperature for 12 hours. The reaction mixture was then filtered to remove any undissolved salt. The filtrate was subjected to distillation to remove the solvent under vacuum at <40° C. The crude product was washed with acetone and n-heptane. The purified product was dried under vacuum at <40° C. and identified by spectral analysis as Zinc Di-(di-n-butyryl lysinate).

Example 4: Preparation of Zinc Di-(di-isobutyryl Lysinate)

Zinc di-(di-isobutyryl lysinate) is prepared according the same procedure as set forth in Example 3 with the exception that di-isobutyryl lysinate of Example 2 is substituted for di-n-butyryl lysinate.

Example 5: Preparation of Calcium Di-(di-n-butyryl Lysinate)

Dibutyryl lysine (2 moles) from Example 1 was mixed with methanol and Calcium hydroxide (1.1 moles) and heated to 65° C. and the mixture maintained at that temperature for 12 hours. The reaction mixture was then filtered to remove any undissolved salt. The filtrate was subjected to distillation to remove the solvent under vacuum at <40° C. The crude product was washed with acetone and n-heptane. The purified product was dried under vacuum at <40° C. and identified by spectral analysis as calcium di-(di-n-butyryl lysinate).

Example 6: Preparation of Calcium Di-(di-isobutyryl Lysinate)

Calcium di-(di-isobutyryl lysinate) is prepared according the same procedure as set forth in Example 5 with the exception that di-isobutyryl lysinate of Example 2 is substituted for di-n-butyryl lysinate.

Example 7: Microphthalmia-associated Transcription Factor (MITF) Expression

DNA Microarray

EpiDermFT tissues were obtained from MatTek and equilibrated overnight in the cell culture incubator. The following day, tissue samples were placed in individual vessels and 3 µl of a 100 µg/ml solution of one of zinc di-n-butyryl lysinate (ZDBL), lysine, Ca lysinate, Zn lysinate and Ca di-n-butyryl lysinate was applied to each tissue sample: each sample was prepared in triplicate. All stock solutions were prepared at 20 mg/ml in DMSO and further dilutions were made in sterile distilled water. The proposed dosage used was based on cytotoxicity data. Water was used as the negative control. The treated tissue samples were incubated for a period of 24 hours following which RNA was extracted and prepared for transcriptome analysis for assessing the impact, if any, on the gene expression of microphthalmia-associated transcription factor (MITF). The results are presented in Table 3. Sequencing data were generated by Azenta Life Sciences (HiSeq 2×150 bp). Analyses were performed using raw FastQ files provided by Azenta.

MITF Gene Expression

As shown in Table 3, the expression of MITF was uniquely suppressed by ZDBL treatment but was not significantly altered by lysine and other three lysine derivatives, namely, Ca lysinate, Zn lysinate and Ca di-n-butyryl lysinate.

TABLE 3

| | MITF Gene Expression Effect |
|---|---|
| Compound | Fold change/mean FPKM* = 2.2 |
| Control | 0.72 |
| Lysine (LYS) | 0.38/No effect |
| Ca lysinate (CLY) | −0.21/No effect |
| Zn lysinate (ZLY) | 0.17/No effect |

TABLE 3-continued

MITF Gene Expression Effect

| Compound | Fold change/mean FPKM* = 2.2 |
|---|---|
| Ca di-(di-n-butyryl lysinate) (CDBL) | 0.41/No effect |
| Zn di-(di-n-butyryl lysinate) (ZDBL) | −1.46; Highly significant reduction in MITF gene; Statistically significance (p = <0.000) |

*FPKM (Fragments Per Kilobase Million)

MITF Gene Expression Validated by PCR

As validation of the findings above a second analysis of the tissue samples was performed this time using cDNA prepared using High-Capacity RNA-to-cDNA™ Kit (Thermo Fisher Scientific). Expression of the applicable genes was measured by real-time quantitative PCR with the BioRad iCycler iQ Detection System using PCR primers from Realtimeprimers (Elkins Park, PA) and AzuraView GreenFast qPCR Blue Mix LR (Azura Genomics, Raynham, MA). Efficiency ΔΔCt method was used for quantification of results, after the normalization of gene expression to GAPD (a housekeeping gene). Genes were considered differentially expressed if the p value, as determined by the two-tailed t-test, was ≤0.10, the modulation was ≥1.7 and the expression level was high (<30 cycles required for detection). The results are summarized in Table 4.

TABLE 4

MITF gene expression validated by PCR

| Compound | Fold change* with p values | Comments |
|---|---|---|
| Ca lysinate | 0.88 (p = 0.115) | No Effect |
| Zn lysinate | 0.98 (p = 0.667) | No Effect |
| Ca di-(di-n-butyryl lysinate) | 0.98 (p = 0.809) | No Effect |
| Zn di-(di-n-butyryl lysinate) | 0.48 (p = 0.001) | Highly significant reduction of MITF gene |

*versus water control

Example 8: Thioredoxin Reductase 1 (TrxR1) Inhibitory Activity

Thioredoxin is known to influence melanogenesis substrates [Y Lu et al., Modulating skin colour: role of thioredoxin and glutathione systems in regulating melanogenesis, Bioscience Reports, 2021; 41 BSR20210427]. Accordingly, a study was undertaken to assess the impact, if any, of zinc di-(di-n-butyryl lysinate) (ZDBL), Ca di-(di-n-butyryl lysinate) and combinations thereof on the inhibition of thioredoxin reductase. Test materials were prepared by dissolving 0.01 gm of each test material in 1 ml ethanol to make stock solutions. For the analysis, 1 to 4 serial dilutions of the stock solutions using buffer (100 mM Potassium phosphate pH 7.0 containing 10 nM EDTA) were prepared to determine the $IC_{50}$ values. Thioredoxin reductase 1 (Raybiotech, Catalog #228-12536-2) was added to the sample and the mixture was incubated for 1 hour at room temperature. After incubation, the working buffer (Phosphate buffer containing 2 mM DTNB and 0.2 mM NADPH) was added. The plate was read at 412 nm for 30 minutes to determine the inhibition. The results are summarized in Table 5.

TABLE 5

Thioredoxin Reductase 1 Inhibitory Activity

| Compound | $IC_{50}$ value in µg/ml* |
|---|---|
| Zn di-(di-n-butyryl lysinate) (ZDBL) | 5.95 |
| Ca di-(di-n-butyryl lysinate) (CDBL) | 4.53 |
| ZDBL:CDBL (1:1 weight ratio) | 5.28 |

*Average of two readings

The results shown in Table 3 indicate that ZDBL, CDBL and the combination of the two have similar impact on the inhibition of thioredoxin reductase 1 enzyme.

Example 9: Tyrosinase Inhibitory Activity

A further study was undertaken to assess the inhibitory effect of Zn di-(di-n-butyryl lysinate) (ZDBL), Ca di-(di-n-butyryl lysinate (CDBL), and Zn lysinate on tyrosinase: tyrosinase being a key enzyme in the production of melanin. Stock solutions of the test compounds were prepared at 20 mg/ml in DMSO: further dilutions were made with sterile distilled water. Sterile distilled water was the negative control and kojic acid (200 µM in distilled water, Sigma Aldrich, St. Louis, MO, catalog #K3125) was employed as the positive control/reference substance. Samples were tested in triplicates using an in vitro tyrosinase inhibition assay based on methods by Pomerantz [Biochem Biophys Res Commun., 16 (2): 188-94, 1964] and Ohguchi et al. [Biosci Biotechnol Biochem, 67:1587-1589, 2003]. Briefly, mushroom tyrosinase (Sigma #31281630) stock solution was prepared in PBS (phosphate buffered saline) at 2000 U/ml and stored at −20° C. in 1 ml aliquots. The final concentration used in the assay was 16 U/well (80 U/ml). Tyrosinase substrate L-DOPA (Acros Organics, Fair Lawn, NJ) was used at 5 mM. Reactions were conducted in a 96 well format and were initiated by adding the enzyme to the reaction mix and allowed to react for 80 min. The colorimetric signal ($A_{450\ nm}$) proportional to the L-DOPA conversion to melanin was acquired using the SpectraMax i3x Multi-Mode Detection Platform from Molecular Devices (Sunnyvale, CA). The increase of the melanin output was calculated using the formula: $\Delta M = [A_{450\ nm(t=80\ min.)} + \text{Tyrosinase}] - [A_{450\ nm(t=80\ min.)} - \text{Tyrosinase}]$ where ΔM is increase of melanin, A is absorbance for a given experimental condition, t is a time point and 450 nm is the wavelength used for the quantification of melanin and "-Tyrosinase" is the background reading of identical experimental conditions without the enzyme. Statistically significant variation was defined as >25% deviation from the water control with p value <0.05 calculated with double-tailed t-test. The results are summarized in Table 6.

As evident from the results in Table 6, Zn di-(di-n-butyryl lysinate) was found to be very effective in inhibiting Tyrosinase activity, particularly at the higher concentrations, whereas the structurally similar analogs-Ca di-(di-n-butyryl lysinate) and Zn lysinate were found to be ineffective.

TABLE 6

Tyrosinase Inhibitory Activity

| Compound/Amount Used | Tyrosinase enzyme activity (% of Control)* | | |
|---|---|---|---|
| | 200 µg/ml | 50 µg/ml | 10 µg/ml |
| Zn di-(di-n-butyryl lysinate) (ZDBL) | 37 (p = 0.00) | 64 (p = 0.00) | 107 (p = 0.36) |
| Ca di-(di-n-butyryl lysinate) (CDBL) | 99 (p = 0.86) | 89 (p = 0.13) | 85 (p = 0.10) |
| Zn lysinate (ZnLys) | 90 (p = 0.23) | 90 (p = 0.95) | 80 (p = 0.02) |

*Kojic acid (200 µM) was used as a positive control: Tyrosinase enzyme activity was found to be 39% of control (p = 0.00) confirming the validation of the protocol.

Example 10: NADPH Oxidase (NOX-4) Inhibitory Activity

A study was conducted on the direct impact of Zn di-(di-n-butyryl lysinate) (ZDBL), Ca di-(di-n-butyryl lysinate), and Na butyrate on NADPH Oxidase 4 (NOX-4) enzyme. In this study, 0.01 gram of sample was dissolved in 1 ml propanediol to make solution. For the analysis, a 1 to 2 serial dilution of the stock solution of the sample using buffer was made to determine the $IC_{50}$ values. The analysis was done following NOX4 ELISA kit (My BioSource, Catalog #MBS2505108) protocol. Results are summarized in Table 7.

TABLE 7

NADPH Oxidase (NOX-4) Inhibitory Activity

| Compound | $IC_{50}$ value in µg/ml |
|---|---|
| Zn di-(di-n-butyroyl lysinate) (ZDBL) | 205 |
| Ca di-(di-n-butyroyl lysinate) (CDBL) | 240 |
| Na butyrate | 170 |

The results shown in Table 7 indicate that ZDBL, CDBL and Na butyrate have similar impact on the inhibition of NOX-4 enzyme activity.

Example 11: Melanin Synthesis

A study was conducted on the direct impact of Zn di-(di-n-butyryl lysinate) (ZDBL), Ca d-(di-n-butyryl lysinate), and Zn Lysinate on melanin production in melanocytes. In this study, B16-F1 melanocytes (cat. #CRL-6323, ATCC, Manassas, VA) were plated in DMEM supplemented with 10% FBS at 10,000 cells/well and the test materials were added 24 hours later. Stock solutions of the test materials were prepared at 20 mg/ml in DMSO with further dilutions made with sterile distilled water immediately before being added to the test cells. Hexylresorcinol (lot #25071VSP10420422) from Sytheon Ltd of Parsippany, NJ was used as the positive reference substance. Three days following the addition of the test materials, the cells were observed through a Nikon Eclipse TS100 inverted microscope and pigmentation was assessed using the Cusabio melanin colorimetric competitive ELISA assay from Lifeome, Oceanside, CA (cat. #E14051h). A Molecular Devices microplate spectrophotometer MAX190 was used to acquire the colorimetric signals and SoftMax3.1.2PRO software was employed to process the signals. p values representing statistical significance were calculated using paired t-test and the threshold of statistical significance being fixed at p=0.05 and a 15% difference as compared to the water control group. The results are summarized in Table 8.

TABLE 8

Inhibition of Melanin Synthesis

| Compound/Amount Used | % Melanin Inhibition** | |
|---|---|---|
| | 200 µg/ml | 50 µg/ml |
| Zn di-(di-n-butyryl lysinate) (ZDBL) | 51 (p = 0.00) | 0 |
| Ca di-(di-n-butyryl lysinate) (CDBL) | 0 | Not done |
| Zn lysinate (ZnLys) | 0 | Not done |

*Water used as a control-Melanin content 100 (p = 1.00)
**Hexylresorcinol (5 µg/ml) was used as a positive control: Melanin inhibition was found fo be 17% of control (p = 0.007) confirming the validation of the protocol.

Microscopic observation did not yield any obvious signs of cytotoxicity, as defined by cell rounding and/or detachment. Colorimetric quantification demonstrated that Zn di-(di-n-butyryl lysinate) at 200 µg/ml had a statistically significant melanin-inhibitory activity whereas ZnLys and CDBL had no significant effect on melanin inhibition. Hexylresorcinol had a mild but statistically significant inhibitory activity technically validating the experiment.

Formulations

As noted above, compositions containing the zinc dibutyryl lysinate component may take any of a number of different forms, both physical form and formulated form, i.e., as neat formulation of the zinc dibutyryl lysinate component in a carrier or as a more multifaceted topical treatment composition. The following presents a number of suitable formulations.

Formulation 1: Skin Lightening Lotion

This formulation is prepared by first adding the components of Phase A to a main kettle equipped with a homogenizer. Thereafter, the Phase B components are slowly sprinkled into the Phase A material. Once the former is fully dispersed in the latter, the mixture is heated to 65-70° C. Concurrently, the components of Phase C are placed and mixed in a side kettle and heated to 70-75° C. Once both mixtures are to the proper temperatures, Phase C is added to the Phase AB mix and the mixture mixed for 15-20 minutes. Concurrently, the components of Phase D are combined in a side kettle and heated to 75° C. Once the zinc dibutyryl lysinate component is dissolved, Phase D is added to the combined Phase ABC and mixed for 5-10 minutes. Once the mixture is homogenous, mixing is switched to side sweep mixing and the mixture allowed to cool to room temperature. Notes: pH—4.5-5.0; Viscosity: Spindle-TE, S95; Speed—0.3 rpm; Range—200,000-500,000 mPas

| Formulation 1 | | |
|---|---|---|
| INCI name | Trade Name/Supplier | % w/w |
| Phase A | | |
| Water | | 71.50 |
| Glycerin | Glycerin/Acme-Hardesty | 2.00 |
| Phenoxyethanol | Jeechem Phenoxy/Jeen | 1.00 |
| Water & Citric Acid | 10% Citric Acid Sln/Jungbunzlauer | 0.75 |
| Trisodium Ethylenediamine Disuccinate | Natrlquest E30/Innospec | 0.10 |

-continued

| Formulation 1 | | |
|---|---|---|
| INCI name | Trade Name/Supplier | % w/w |
| Phase B | | |
| Xanthan Gum | Vanzan NF/Vanderbilt | 0.40 |
| Hydroxyethyl Acrylate/Sodium Acryloyldimethyl Taurate Copolymer | Sepinov EMT 10/Seppic | 1.00 |
| Phase C | | |
| Helianthus Annuus (Sunflower) Seed Oil | Sunflower Oil/Jeen | 5.00 |
| Tocopheryl Acetate | Vitamin E Acetate/Jeen | 0.25 |
| Cetearyl Alcohol & Ceteareth-20 | Ritapro 300/Rita | 2.50 |
| Potassium Cetyl Phosphate | Amphisol K/DSM | 1.50 |
| Butyrospermum Parkii (Shea) Butter | Shebu Refined/Rita | 2.00 |
| Isosorbide Dicaprylate | Hydra Synol ® DOI/Sytheon | 2.00 |
| Phase D | | |
| Butylene Glycol | Jeechem BUGL/Jeen | 8.00 |
| Zinc di-(di-n-butyryl lysinate) or Zinc di-(di-isobutyryl lysinate) | Sytheon | 2.00 |
| Total | | 100.00 |

Formulation 2: Moisturizing and Skin Lightening Serum

Formulation 2 is prepared by combining the Phase A ingredients in a kettle equipped with a homogenizer and mixed. As Phase A is being mixed, the components of Phase B are sprinkled in and the combination mixed until uniform. Concurrently, the components of Phase C are mixed in a side kettle until uniform and then added to the Phase AB mix and this mixture mixed for 10-15 minutes. The Phase D ingredients are combined in a in a side kettle and heated to 75° C. to dissolve the zinc dibutyryl lysinate component. Once dissolved, heating is stopped and the mixture allowed to cool to room temperature following which it is added to the Phase ABC mix and the mixture mixed for 5-10 minutes. Notes: pH-5.5-6.0; Viscosity: Spindle-TD, S94; Speed-2.0 rpm; Range-8,000-11,000 mPas.

| Formulation 2 | | |
|---|---|---|
| INCI name | Trade Name/Supplier | % w/w |
| Phase A | | |
| Water | | 76.65 |
| Glycerin | Glycerin/Acme-Hardesty | 3.00 |
| Water & Potassium Sorbate & Sodium Benzoate | Euxyl K 712/Schulke | 1.00 |
| Water & Citric Acid | 10% Citric Acid Sln/Jungbunzlauer | 1.00 |
| Trisodium Ethylenediamine Disuccinate | Natrlquest E30/Innospec | 0.10 |
| Phase B | | |
| Acacia Senegal Gum & Xanthan Gum | Solagum AX/Seppic | 0.50 |
| Hydroxyethyl Acrylate/Sodium Acryloyldimethyl Taurate Copolymer | Sepinov EMT 10/Seppic | 1.50 |

-continued

| Formulation 2 | | |
|---|---|---|
| INCI name | Trade Name/Supplier | % w/w |
| Phase C | | |
| Helianthus Annuus (Sunflower) Seed Oil | Sunflower Oil/Jeen | 3.00 |
| Isostearyl Alcohol & Butylene Glycol Cocoate & Ethylcellulose | Emulfree CBG/Gattefosse | 1.00 |
| Isosorbide Dicaprylate | Hydra Synol ® DOI/Sytheon | 3.00 |
| Phase D | | |
| Propanediol | Zemea/DuPont | 8.00 |
| Zinc di-(di-n-butyryl lysinate) or Zinc di-(di-isobutyryl lysinate) | Sytheon | 2.00 |
| Total | | 100.00 |

Formulation 3: Skin Even Toning Lotion with Hexylresorcinol

Formulation 3 is prepared by first adding the components of Phase A to a main kettle equipped with a homogenizer. Thereafter, the Phase B components are slowly sprinkled into the Phase A material. Once the former is fully dispersed in the latter, the mixture is heated to 65-70° C. Concurrently, the components of Phase C are placed and mixed in a side kettle and heated to 70-75° C. Once both mixtures are to the proper temperatures, Phase C is added to the Phase AB mix and the mixture mixed for 15-20 minutes. Concurrently, combine the first two components of Phase D in a side kettle and heat to 75° C. Once the zinc dibutyryl lysinate component is dissolved the mixture is cooled to 45° C. and the hexylresorcinol is added and mixed until uniform. The combined Phase ABC mix is then switched to side sweep mixing and the mixture allowed to cool 45° C. Thereafter, Phase D is added to the Phase ABC mix and mixed for 5-10 minutes and the total mixture allowed to cool to room temperature. Notes: pH-4.5-5.0; Viscosity: Spindle-TE, S95; Speed-0.3 rpm; Range-200,000-500,000 mPas.

| Formulation 3 | | |
|---|---|---|
| INCI name | Trade Name/Supplier | % w/w |
| Phase A | | |
| Water | | 70.00 |
| Glycerin | Glycerin/Acme-Hardesty | 2.00 |
| Phenoxyethanol | Jeechem Phenoxy/Jeen | 1.00 |
| Water & Citric Acid | 10% Citric Acid Sln/Jungbunzlauer | 0.75 |
| Trisodium Ethylenediamine Disuccinate | Natrlquest E30/Innospec | 0.10 |
| Phase B | | |
| Xanthan Gum | Vanzan NF/Vanderbilt | 0.40 |
| Hydroxyethyl Acrylate/Sodium Acryloyldimethyl Taurate Copolymer | Sepinov EMT 10/Seppic | 1.00 |
| Phase C | | |
| Helianthus Annuus (Sunflower) Seed Oil | Sunflower Oil/Jeen | 5.00 |
| Tocopheryl Acetate | Vitamin E Acetate/Jeen | 0.25 |
| Cetearyl Alcohol & Ceteareth-20 | Ritapro 300/Rita | 2.50 |
| Potassium Cetyl Phosphate | Amphisol K/DSM | 1.50 |
| Butyrospermum Parkii (Shea) Butter | Shebu Refined/Rita | 2.00 |
| Isosorbide Dicaprylate | Hydra Synol ® DOI/Sytheon | 2.00 |

-continued

| Formulation 3 | | |
|---|---|---|
| INCI name | Trade Name/Supplier | % w/w |
| Phase D | | |
| Butylene Glycol | Jeechem BUGL/Jeen | 8.00 |
| Zinc di-(di-n-butyryl lysinate) or Zinc di-(di-isobutyryl lysinate) | Sytheon | 2.00 |
| Hexylresorcinol | Synovea ® HR/Sytheon | 0.50 |
| Total | | 100.00 |

Formulation 4: Skin Brightening Lotion with Bakuchiol

Formulation 4 is prepared by first adding the components of Phase A to a main kettle equipped with a homogenizer. Thereafter, the Phase B components are slowly sprinkled into the Phase A material. Once the former is fully dispersed in the latter, the mixture is heated to 65-70° C. Concurrently, the components of Phase C are placed and mixed in a side kettle and heated to 70-75° C. Once both mixtures are to the proper temperatures, Phase C is added to the Phase AB mix and the mixture mixed for 15-20 minutes. Concurrently, the components of Phase D are combined in a side kettle and heated to 75° C. Once the zinc dibutyryl lysinate component is dissolved, Phase D is added to the combined Phase ABC and mixed for 5-10 minutes. Once the mixture is homogenous, mixing is switched to side sweep mixing and the mixture allowed to cool to room temperature. Notes: PH-4.8-5.0 Viscosity: Spindle-TE, 895; Speed-0.3 rpm; Range-200,000-500,000 mPas.

| Formulation 4 | | |
|---|---|---|
| INCI name | Trade Name/Supplier | % w/w |
| Phase A | | |
| Water | | 70.50 |
| Glycerin | Glycerin/Acme-Hardesty | 2.00 |
| Phenoxyethanol | Jeechem Phenoxy/Jeen | 1.00 |
| Water & Citric Acid | 10% Citric Acid Sln/Jungbunzlauer | 0.75 |
| Trisodium Ethylenediamine Disuccinate | Natrlquest E30/Innospec | 0.10 |
| Phase B | | |
| Xanthan Gum | Vanzan NF/Vanderbilt | 0.40 |
| Hydroxyethyl Acrylate/Sodium Acryloyldimethyl Taurate Copolymer | Sepinov EMT 10/Seppic | 1.00 |
| Phase C | | |
| Helianthus Annuus (Sunflower) Seed Oil | Sunflower Oil/Jeen | 5.00 |
| Tocopheryl Acetate | Vitamin E Acetate/Jeen | 0.25 |
| Cetearyl Alcohol & Ceteareth-20 | Ritapro 300/Rita | 2.50 |
| Potassium Cetyl Phosphate | Amphisol K/DSM | 1.50 |
| Butyrospermum Parkii (Shea) Butter | Shebu Refined/Rita | 2.00 |
| Isosorbide Dicaprylate | Hydra Synol ® DOI/Sytheon | 2.00 |
| Bakuchiol | Sytenol ® A/Sytheon | 1.00 |
| Phase D | | |
| Butylene Glycol | Jeechem BUGL/Jeen | 8.00 |
| Zinc di-(di-n-butyryl lysinate) or Zinc di-(di-isobutyryl lysinate) | Sytheon | 2.00 |
| Total | | 100.00 |

Formulation 5: Skin Lightening Lotion

Formulation 5 is prepared according to the same method as Formulation 4.

| Formulation 5 | | |
|---|---|---|
| INCI name | Trade Name/Supplier | % w/w |
| Phase A | | |
| Water | | 65.50 |
| Glycerin | Glycerin/Acme-Hardesty | 2.00 |
| Phenoxyethanol | Jeechem Phenoxy/Jeen | 1.00 |
| Water & Citric Acid | 10% Citric Acid Sln/Jungbunzlauer | 0.75 |
| Trisodium Ethylenediamine Disuccinate | Natrlquest E30/Innospec | 0.10 |
| Phase B | | |
| Xanthan Gum | Vanzan NF/Vanderbilt | 0.40 |
| Hydroxyethyl Acrylate/Sodium Acryloyldimethyl Taurate Copolymer | Sepinov EMT 10/Seppic | 1.00 |
| Phase C | | |
| Helianthus Annuus (Sunflower) Seed Oil | Sunflower Oil/Jeen | 5.00 |
| Tocopheryl Acetate | Vitamin E Acetate/Jeen | 0.25 |
| Cetearyl Alcohol & Ceteareth-20 | Ritapro 300/Rita | 2.50 |
| Potassium Cetyl Phosphate | Amphisol K/DSM | 1.50 |
| Butyrospermum Parkii (Shea) Butter | Shebu Refined/Rita | 2.00 |
| Isosorbide Dicaprylate | Hydra Synol ® DOI/Sytheon | 2.00 |
| Acetyl Zingerone | Synoxyl ® AZ/Sytheon | 1.00 |
| Phenethyl Benzoate | X-Tend 226/Ashland | 5.00 |
| Phase D | | |
| Butylene Glycol | Jeechem BUGL/Jeen | 8.00 |
| Zinc di-(di-n-butyryl lysinate) or Zinc di-(di-isobutyryl lysinate) | Sytheon | 2.00 |
| Total | | 100.00 |

Formulation 6: Skin Lightening Lotion with Pollution and Blue Light Protection Benefits Formulation 6 is prepared by first adding the components of Phase A to a main kettle equipped with a homogenizer. Thereafter, the Phase B components are slowly sprinkled into the Phase A material. Once the former is fully dispersed in the latter, the mixture is heated to 65-70° C. Concurrently, the components of Phase C are placed and mixed in a side kettle and heated to 70-75° C. Once both mixtures are to the proper temperatures, Phase C is added to the Phase AB mix and the mixture mixed for 15-20 minutes. Concurrently, the components of Phase D are combined in a side kettle and heated to 75° C. Once the zinc dibutyryl lysinate component is dissolved, Phase D is added to the combined Phase ABC and mixed for 5-10 minutes. The combined Phase ABC mix is then switched to side sweep mixing and the mixture allowed to cool 45° C. Concurrently, the water component of Phase E is added to a separate kettle and heated to 45° C. whereupon the Terminalia Chebula extract is added and mixed until dissolved. Thereafter, Phase E is added to the Phase ABCD mix and mixed until uniform and then the batch allowed to cool to room temperature. Notes: pH-4.5-5.0; Viscosity: Spindle-TE, S95; Speed-0.3 rpm; Range-200,000-500,000 mPas.

Formulation 6

| INCI name | Trade Name/Supplier | % w/w |
|---|---|---|
| Phase A | | |
| Water | | 68.00 |
| Glycerin | Glycerin/Acme-Hardesty | 2.00 |
| Phenoxyethanol | Jeechem Phenoxy/Jeen | 1.00 |
| Water & Citric Acid | 10% Citric Acid Sln/Jungbunzlauer | 0.75 |
| Trisodium Ethylenediamine Disuccinate | Natrlquest E30/Innospec | 0.10 |
| Phase B | | |
| Xanthan Gum | Vanzan NF/Vanderbilt | 0.40 |
| Hydroxyethyl Acrylate/Sodium Acryloyldimethyl Taurate Copolymer | Sepinov EMT 10/Seppic | 1.00 |
| Phase C | | |
| Helianthus Annuus (Sunflower) Seed Oil | Sunflower Oil/Jeen | 5.00 |
| Tocopheryl Acetate | Vitamin E Acetate/Jeen | 0.25 |
| Cetearyl Alcohol & Ceteareth-20 | Ritapro 300/Rita | 2.50 |
| Potassium Cetyl Phosphate | Amphisol K/DSM | 1.50 |
| Butyrospermum Parkii (Shea) Butter | Shebu Refined/Rita | 2.00 |
| Isosorbide Dicaprylate | Hydra Synol ® DOI/Sytheon | 2.00 |
| Phase D | | |
| Butylene Glycol | Jeechem BUGL/Jeen | 8.00 |
| Zinc di-(di-n-butyryl lysinate) or Zinc di-(di-isobutyryl lysinate) | Sytheon | 2.00 |
| Phase E | | |
| Terminalia Chebula Fruit Extract | Synastol ® TC/Sytheon | 0.50 |
| Water | | 3.00 |
| Total | | 100.00 |

Formulation 7 Anti-Aging Cream

Formulation 7 is prepared by combining the Phase A ingredients in a kettle equipped with a homogenizer and mixed. As Phase A is being mixed, the components of Phase B are sprinkled in and the combination mixed until uniform. Concurrently, the components of Phase C are mixed in a side kettle until uniform and then added to the Phase AB mix and this mixture mixed for 10-15 minutes. The Phase D ingredients are combined in a side kettle and mixed until uniform. Once the New Active is dissolved (minor heating may be necessary to facilitate dissolving) Phase D is added to the Phase ABC mix and the mixture mixed for 5-10 minutes. Thereafter, Phase E is added and mixed until uniform. Notes: pH-5.5-6.0; Viscosity: Spindle-TE, S95; Speed-0.3 rpm; Range-400,000-700,000 mPas.

Formulation 7

| INCI name | Trade Name/Supplier | % w/w |
|---|---|---|
| Phase A | | |
| Water | | 71.65 |
| Glycerin | Glycerin/Acme-Hardesty | 2.00 |
| Disodium EDTA | Ronacare EDTA/EMD | 0.10 |
| Water & Citric Acid | 10% Citric Acid Sln/Jungbunzlauer | 0.50 |
| Steareth-2 | Jeecol SA-2/Jeen | 1.25 |
| PEG-8 | Pluracare E 400/BASF | 2.00 |
| Niacinamide | Niacinamide/Lonza | 2.00 |
| Caffeine | Caffeine/EMD | 0.50 |
| Butylene Glycol | Jeechem BUGL/Jeen | 3.00 |
| Caprylyl Glycol & Phenoxyethanol & Hexylene Glycol | Jeecide CAP-2/Jeen | 1.00 |
| Phase B | | |
| Ammonium Acryloyldimethyltaurate/VP Copolymer | Aristoflex AVC/Clariant | 1.00 |
| Phase C | | |
| Cyclopentasiloxane | Xiameter PMX-0245/Dow Corning | 5.00 |
| Dimethicone | Dimethicone Fluid/Making Cosmetics | 1.00 |
| Isosorbide Dicaprylate | Hydra Synol ® DOI/Sytheon | 2.00 |
| Phase D | | |
| Denatured Alcohol | Denatured Alcohol/Quality Chemical | 4.00 |
| Zinc Di-(di-n-butyryl lysinate) | Epi-G-Synol ® Z DBL/Sytheon | 1.00 |
| Phase E | | |
| Hydroxyethyl Acrylate/Sodium Acryloyldimethyl Taurate Copolymer & Squalane & Polysorbate 60 | Simulgel NS/Seppic | 2.00 |
| Total | | 100.00 |

Formulation 8

Formulation 8 is prepared by combining the Phase A ingredients in a kettle equipped with a homogenizer and mixed. As Phase A is being mixed, the components of Phase B are sprinkled in and the combination mixed. Once Phase B is dispersed, the mixture is heated to 65-70° C. Concurrently, the components of Phase C are mixed in a side kettle and heated to 70-75° C. until uniform. Once both Phase AB and Phase C are at the indicated temperatures, Phase C is added to Phase AB and mixed for 15-20 minutes. The Phase D ingredients are combined in a side kettle and mixed until uniform (minor heating may be necessary to facilitate dissolving of the New Active. The Phase ABC mix is changed to a side sweep mixing and cooled to 45° C. and Phase D added with mixing. Phase E is prepared in a side kettle and mixed until uniform. Phase E is then added to the Phase ABCD and mixed for 5-10 minute after which it is cooled to room temperature. Notes: pH-4.5-5.0; Viscosity: Spindle-TE, S95; Speed-0.3 rpm; Range-200,000-500,000 mPas.

Formulation 8

| INCI name | Trade Name/Supplier | % w/w |
|---|---|---|
| Phase A | | |
| Water | | 72.00 |
| Glycerin | Glycerin/Acme-Hardesty | 2.00 |
| Phenoxyethanol | Jeechem Phenoxy/Jeen | 1.00 |
| Water & Citric Acid | 10% Citric Acid Sln/Jungbunzlauer | 0.75 |
| Trisodium Ethylenediamine Disuccinate | Natrlquest E30/Innospec | 0.10 |
| Phase B | | |
| Xanthan Gum | Vanzan NF/Vanderbilt | 0.40 |
| Hydroxyethyl Acrylate/Sodium Acryloyldimethyl Taurate Copolymer | Sepinov EMT 10/Seppic | 1.00 |

| Formulation 8 | | |
|---|---|---|
| INCI name | Trade Name/Supplier | % w/w |
| Phase C | | |
| Helianthus Annuus (Sunflower) Seed Oil | Sunflower Oil/Jeen | 5.00 |
| Tocopheryl Acetate | Vitamin E Acetate/Jeen | 0.25 |
| Cetearyl Alcohol & Ceteareth-20 | Ritapro 300/Rita | 2.50 |
| Potassium Cetyl Phosphate | Amphisol K/DSM | 1.50 |
| Butyrospermum Parkii (Shea) Butter | Shebu Refined/Rita | 2.00 |
| Isosorbide Dicaprylate | Hydra Synol ® DOI/Sytheon | 2.00 |
| Phase D | | |
| Coco-Betaine | Cola Teric CB/Colonial Chemical | 2.00 |
| Cocamidopropyl Betaine | Dehyton PK 45/BASF | 2.00 |
| Zinc Di-(di-n-butyryl lysinate) | Epi-G-Synol ® Z DBL/Sytheon | 1.00 |
| Phase E | | |
| Butylene Glycol | Jeechem BUGL/Jeen | 4.00 |
| Hexylresorcinol | Synovea ® HR/Sytheon | 0.50 |
| Total | | 100.00 |

Formulation 9: Anti-Aging Lotion

Formulation 9 is prepared by combining the Phase A ingredients in a kettle equipped with a homogenizer and mixed. As Phase A is being mixed, the components of Phase B are sprinkled in and the combination mixed. Once Phase B is dispersed, the mixture is heated to 65-70° C. Concurrently, the components of Phase C are mixed in a side kettle and heated to 70-75° C. until uniform. Once both Phase AB and Phase C are at the indicated temperatures, Phase C is added to Phase AB and mixed for 15-20 minutes. The Phase D ingredients are combined in a side kettle and mixed until uniform (minor heating may be necessary to facilitate dissolving of the New Active. The Phase ABC mix is changed to a side sweep mixing and cooled to room temperature. Once at room temperature Phase D is added and mixed for 5-10 minutes. Notes: pH-4.5-5.0; Viscosity: Spindle-TE, S95; Speed-0.3 rpm; Range-200,000-500,000 mPas.

| Formulation 9 | | |
|---|---|---|
| INCI name | Trade Name/Supplier | % w/w |
| Phase A | | |
| Water | | 70.50 |
| Glycerin | Glycerin/Acme-Hardesty | 2.00 |
| Phenoxyethanol | Jeechem Phenoxy/Jeen | 1.00 |
| Water & Citric Acid | 10% Citric Acid Sln/Jungbunzlauer | 0.75 |
| Trisodium Ethylenediamine Disuccinate | Natrlquest E30/Innospec | 0.10 |
| Phase B | | |
| Xanthan Gum | Vanzan NF/Vanderbilt | 0.40 |
| Hydroxyethyl Acrylate/Sodium Acryloyldimethyl Taurate Copolymer | Sepinov EMT 10/Seppic | 1.00 |
| Phase C | | |
| Helianthus Annuus (Sunflower) Seed Oil | Sunflower Oil/Jeen | 5.00 |
| Tocopheryl Acetate | Vitamin E Acetate/Jeen | 0.25 |
| Cetearyl Alcohol & Ceteareth-20 | Ritapro 300/Rita | 2.50 |
| Potassium Cetyl Phosphate | Amphisol K/DSM | 1.50 |
| Butyrospermum Parkii (Shea) Butter | Shebu Refined/Rita | 2.00 |

| Formulation 9 | | |
|---|---|---|
| INCI name | Trade Name/Supplier | % w/w |
| Isosorbide Dicaprylate | Hydra Synol ® DOI/Sytheon | 2.00 |
| Acetyl Zingerone | Synoxyl ® AZ/Sytheon | 1.00 |
| Phenethyl Benzoate | X-Tend 226/Ashland | 5.00 |
| Phase D | | |
| Denatured Alcohol | Denatured Alcohol/Quality Chemical | 4.00 |
| Zinc Di-(di-n-butyryl lysinate) | Epi-G-Synol ® Z DBL/Sytheon | 1.00 |
| Total | | 100.00 |

Without further elaboration, it is believed that one skilled in the art, using the preceding description, can utilize the present invention to its fullest extent. Furthermore, while the present invention has been described with respect to the aforementioned specific embodiments and examples, it should be appreciated that other embodiments, changes and modifications utilizing the concept of the present invention are possible, and within the skill of one in the art, without departing from the spirit and scope of the Invention. The preceding preferred specific embodiments are, therefore, to be construed as merely illustrative, and not limitative of the remainder of the disclosure in any way whatsoever.

I claim:

1. The compound zinc di-(di-n-butyryl lysinate), depicted as Structure 1

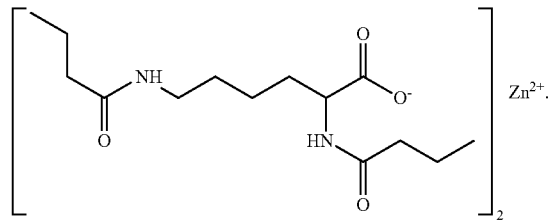

Structure 1

2. The compound zinc di-(di-isobutyryl lysinate), depicted as Structure 2

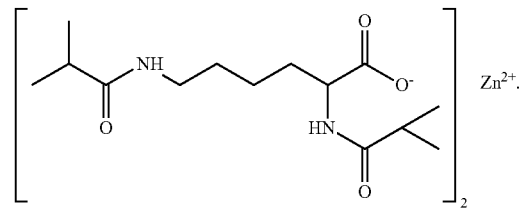

Structure 2

3. A composition comprising (i) a zinc dibutyryl lysinate component selected from zinc di-(di-n-butyryl lysinate), zinc di-(di-isobutyryl lysinate) and a mixture of the two, (ii) optionally, a skin lightening agent that is not (i), and (iii) a dermatologically acceptable carrier.

4. The composition of claim 3 wherein the zinc dibutyryl lysinate component is zinc di-(di-n-butyryl lysinate).

5. The composition of claim 3 wherein the zinc dibutyryl lysinate component is zinc di-(di-isobutyryl lysinate).

6. The composition of claim 3 wherein the skin lightening agent (ii) is present.

7. The composition of claim 6 wherein the skin lightening agent is selected from hexylresorcinol, bakuchiol, acetyl zingerone and combinations of any two or more thereof.

8. The composition of claim 3 wherein the zinc dibutyryl lysinate component is present in an amount of from about 0.05 to about 10 wt % based on the total weight of the composition, the skin lightening agent (ii), if present, is present in an amount of from about 0.05 to about 20 wt % based on the total weight of the composition, and the weight ratio of the zinc dibutyryl lysinate component to the skin lightening agent (ii) is from about 10:1 to about 1:10.

9. The composition of claim 3 wherein the zinc dibutyryl lysinate component is present in an amount of from about 0.1 to about 10 wt % based on the total weight of the composition, the skin lightening agent (ii), if present, is present in an amount of from about 0.1 to about 10 wt % based on the total weight of the composition, and the weight ratio of the zinc dibutyryl lysinate component to the skin lightening agent (ii) is from about 5:1 to about 1:5.

10. The composition of claim 3 further comprising one or more skin protective or treatment ingredients in an effective amount.

11. The composition of claim 10 wherein the one or more skin protective or treatment ingredients are selected from the group consisting of sunscreen actives, antioxidants, vitamins, anti-inflammatory agents, moisturizers, emollients, humectants, and mixtures thereof.

12. The composition of claim 10 wherein the one or more skin protective or treatment ingredients is selected from bakuchiol, isosorbide dicaprylate, terminalia chebula fruit extract, ethyl linoleate, isosorbide dilinoleate, isosorbide disunflowerseedate and mixtures thereof.

13. The composition of claim 3 wherein the dermatological carrier is formulated product or base composition for the production of a formulated product selected from a cosmetic, sunscreen, moisturizer, skin serum, anti-aging composition, acne treatment, general skin care product, rejuvenation product, topical pharmaceutical products, or sunburn treatment.

14. The composition of claim 3 further comprising one or more dermatologically acceptable amphoteric surfactants, ethanol, or a mixture thereof.

15. A method for lightening/brightening/even-toning the color of skin, maintaining skin coloration and even tone, and/or preventing skin discoloration said method comprising applying a composition comprising an effective amount of a zinc dibutyryl lysinate component selected from zinc di-(di-n-butyryl lysinate), zinc di-(di-isobutyryl lysinate) and a mixture of the two to those areas of the skin for which the desired effect is to be attained.

16. The method of claim 15 wherein the composition comprises (i) the zinc dibutyryl lysinate component, (ii) optionally, a skin lightening agent that is not (i), and (iii) a dermatologically acceptable carrier.

17. The method of claim 16 wherein the zinc dibutyryl lysinate component is zinc di-(di-n-butyryl lysinate).

18. The method of claim 16 wherein the skin lightening agent (ii) is present and is selected from hexylresorcinol, acetyl zingerone and a combination of the two.

19. The method of claim 16 wherein the zinc dibutyryl lysinate component is present in an amount of from about 0.05 to about 10 wt % based on the total weight of the composition, the skin lightening agent (ii), if present, is present in an amount of from about 0.05 to about 20 wt % based on the total weight of the composition, and the weight ratio of the zinc dibutyryl lysinate component to the skin lightening agent (ii) is from about 10:1 to about 1:10.

20. The method of claim 15 wherein the composition is applied to all or essentially all areas of the skin to affect an overall skin lightening/brightening/even-toning thereof.

21. The method of claim 15 wherein the composition is applied to those areas of the skin manifesting hyperpigmentation and/or an uneven or blotched skin coloring.

* * * * *